United States Patent
Sawyer et al.

(10) Patent No.: US 8,119,849 B2
(45) Date of Patent: Feb. 21, 2012

(54) PROPYLENE PRODUCTION

(75) Inventors: Gary A. Sawyer, Media, PA (US); Michael G. Axelrod, Newtown Square, PA (US)

(73) Assignee: Lyondell Chemical Technology, L.P., Houston, TX (US)

( * ) Notice: Subject to any disclaimer, the term of this patent is extended or adjusted under 35 U.S.C. 154(b) by 491 days.

(21) Appl. No.: 12/317,794

(22) Filed: Dec. 29, 2008

(65) Prior Publication Data
US 2010/0168487 A1    Jul. 1, 2010

(51) Int. Cl.
*C07C 6/04* (2006.01)
*C07C 5/27* (2006.01)

(52) U.S. Cl. .......... 585/324; 585/643; 585/671

(58) Field of Classification Search ........... 585/324, 585/643, 671
See application file for complete search history.

(56) References Cited

U.S. PATENT DOCUMENTS

| | | |
|---|---|---|
| 2,471,647 A | 5/1949 | Oblad et al. |
| 3,558,733 A | 1/1971 | Myers et al. |
| 4,242,530 A | 12/1980 | Smith, Jr. |
| 4,513,099 A | 4/1985 | Kukes et al. |
| 4,992,612 A | 2/1991 | Suzukamo et al. |
| 4,992,613 A | 2/1991 | Brownscombe |
| 5,120,894 A | 6/1992 | McCauley |
| 5,153,165 A | 10/1992 | Lowery et al. |
| 5,300,718 A | 4/1994 | McCaulley |
| 5,321,195 A | 6/1994 | Travers et al. |
| 5,659,104 A | 8/1997 | Travers et al. |
| 5,817,907 A | 10/1998 | Benazzi et al. |
| 6,111,160 A | 8/2000 | Powers et al. |
| 6,586,649 B1 | 7/2003 | Botha et al. |
| 6,743,958 B2 | 6/2004 | Commereuc et al. |
| 6,872,862 B2 | 3/2005 | Bridges et al. |
| 6,977,318 B2 | 12/2005 | Bridges |
| 7,074,976 B2 | 7/2006 | Powers et al. |
| 7,214,841 B2 | 5/2007 | Gartside et al. |
| 2002/0019307 A1 | 2/2002 | Benazzi et al. |
| 2003/0004385 A1 | 1/2003 | Gartside et al. |
| 2004/0249229 A1 | 12/2004 | Gee et al. |
| 2005/0250969 A1 * | 11/2005 | Bridges .................. 585/324 |
| 2006/0084831 A1 | 4/2006 | Zhang |
| 2007/0129589 A1 | 6/2007 | Iwamoto et al. |
| 2008/0154077 A1 | 6/2008 | Bozzano et al. |

FOREIGN PATENT DOCUMENTS
EP    0 050 157    4/1982

OTHER PUBLICATIONS

"Butylenes," *Kirk-Othmer Encyclopedia of Chemical Technology*, John Wiley & Sons, Inc., 2008, pp. 402-433.

* cited by examiner

Primary Examiner — Thuan Dinh Dang

(57) ABSTRACT

A propylene production process is disclosed. The process comprises (a) reacting a feed stream comprising isobutene in the presence of a skeletal isomerization catalyst to obtain an isomerized stream comprising $C_4$ olefins; and (b) reacting the isomerized stream with ethylene in the presence of a metathesis catalyst to form a metathesis product stream comprising propylene, $C_4$ olefins, and $C_5+$ olefins. The metathesis reaction pressure is equal to or lower than that of the skeletal isomerization.

13 Claims, 2 Drawing Sheets

PROPYLENE PRODUCTION

FIELD OF THE INVENTION

The invention relates to a process for producing propylene from a $C_4$ olefin and ethylene.

BACKGROUND OF THE INVENTION

Steam cracking of hydrocarbons is a petrochemical process that is widely used to produce olefins such as ethylene, propylene, $C_4$ olefins (1-butene, 2-butenes, isobutene), butadiene, and aromatics such as benzene, toluene, and xylene. 2-Butenes include cis-2-butene and/or trans-2-butene. In an olefin plant, a hydrocarbon feedstock such as naphtha, gas oil, or other fractions of whole crude oil is mixed with steam. This mixture, after preheating, is subjected to severe thermal cracking at elevated temperatures in a pyrolysis furnace. The cracked effluent from the pyrolysis furnace contains gaseous hydrocarbons of great variety (from 1 to 35 carbon atoms per molecule). This effluent contains hydrocarbons that are aliphatic, aromatic, saturated, and unsaturated, and may contain significant amounts of molecular hydrogen. The cracked product of a pyrolysis furnace is then further processed in the olefin plant to produce, as products of the plant, various individual product streams such as hydrogen, ethylene, propylene, mixed hydrocarbons having four or five carbon atoms per molecule, and pyrolysis gasoline.

Crude $C_4$ hydrocarbons can contain varying amounts of n-butane, isobutane, $C_4$ olefins, acetylenes (ethyl acetylene and vinyl acetylene), and butadiene. See *Kirk-Othmer Encyclopedia of Chemical Technology*, online edition (2008). Crude $C_4$ hydrocarbons are typically subjected to butadiene extraction or butadiene selective hydrogenation to remove most, if not essentially all, of the butadiene and acetylenes present. Thereafter the $C_4$ raffinate (called raffinate-1) is subjected to a chemical reaction (e.g., etherification, hydration, or dimerization) wherein the isobutene is converted to other compounds (e.g., methyl tert-butyl ether, tert-butyl alcohol, or diisobutene) (see, e.g., U.S. Pat. Nos. 6,586,649 and 4,242,530). The remaining $C_4$ stream containing mainly n-butane, isobutane, 1-butene and 2-butenes is called raffinate-2. However, sometimes the market demand for methyl tert-butyl ether, tert-butyl alcohol, or diisobutene is limited and it is desirable to convert isobutene into other valuable products, such as propylene.

Processes for producing propylene by isobutene skeletal isomerization and metathesis reactions are known. See, e.g., U.S. Pat. Nos. 6,743,958, 6,872,862, 6,977,318, 7,074,976. Skeletal isomerization is practiced at relatively low pressures to limit undesirable side reactions. However, the processes disclosed so far require the metathesis step to be performed at relatively high pressure. As a result, it is necessary to cool the isomerized stream from the skeletal isomerization to a lower temperature in order to pressurize the stream, then heat the stream to a high temperature before it is fed to the metathesis reaction. In an example in U.S. Pat. No. 6,743,958, the metathesis reactor is operated at 3.5 MPa (514 psig). U.S. Pat. Nos. 6,872,862, 6,977,318, and 7,074,976 teach that the metathesis reaction is performed at a temperature of 300 to 800 F and under a pressure of 200 to 600 psig.

It is desirable to develop processes that minimize the heat-exchanging requirements and thus energy and equipment costs.

SUMMARY OF THE INVENTION

The invention is propylene production process. The process comprises (a) reacting a feed stream comprising isobutene in the presence of a skeletal isomerization catalyst to obtain an isomerized stream comprising $C_4$ olefins; and (b) reacting the isomerized stream with ethylene in the presence of a metathesis catalyst to form a metathesis product stream comprising propylene, $C_4$ olefins, and $C_5$ and higher olefins. The metathesis reaction pressure is equal to or lower that of the skeletal isomerization.

DETAILED DESCRIPTION OF THE INVENTION

Figure 1:
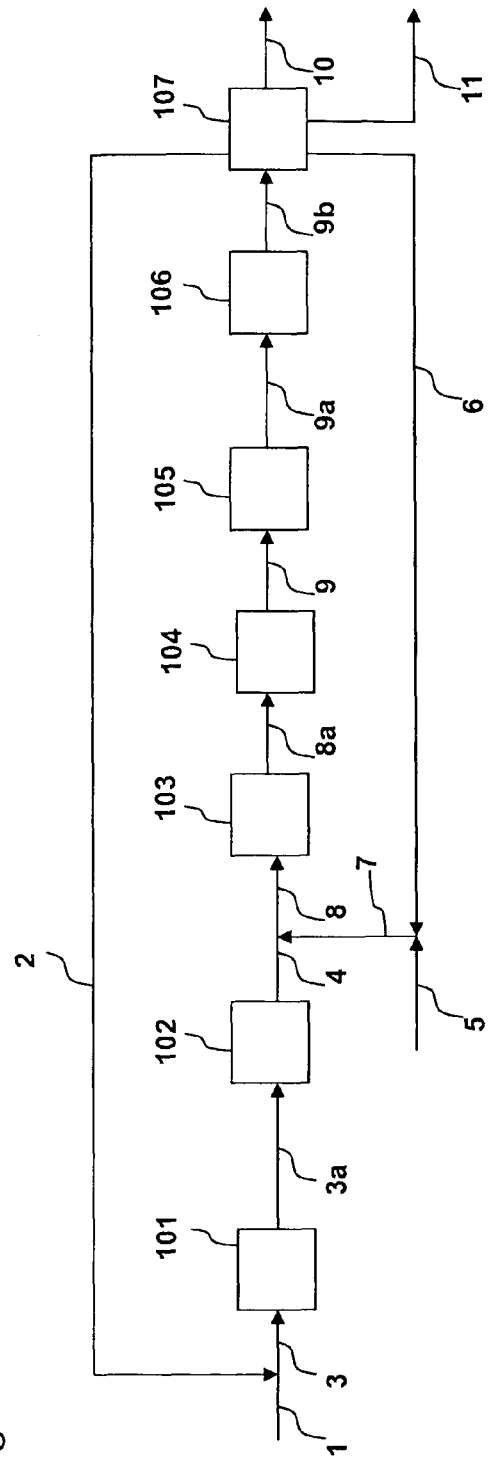
FIG. 1 is a schematic representation of one embodiment of the invention.

The feed stream of the process comprises isobutene. Preferably, the feed comprises greater than 95 wt % $C_4$ olefins. One suitable feed stream may be obtained from raffinate-1, which is obtained from a crude $C_4$ stream from refining or steam cracking processes. Raffinate-1 contains mostly $C_4$ olefins, n-butane, and isobutane. Preferably, paraffins (n-butane and isobutane) are removed from raffinate-1 by extractive distillation with a suitable extractive solvent (e.g., dimethyl formamide, N-methylpyrrollidone, or N-formyl morpholine) or selective adsorption. One suitable feed is obtained by dehydration of tert-butyl alcohol.

The process comprises reacting the feed stream in the presence of a skeletal isomerization catalyst to obtain an isomerized stream comprising $C_4$ olefins. The skeletal isomerization catalyst is any solid that can catalyze isomerization of isobutene to linear $C_4$ olefins (1-butene, 2-butenes). Additionally, they also catalyze the conversion between 1-butene and 2-butenes. These catalysts are known in the art. Suitable skeletal isomerization catalysts include zeolites, metal oxides, and mixed metal oxides.

A skeletal isomerization catalyst comprising a zeolite may be used. Zeolites generally contain one or more of Si, Ge, Al, B, P, or the like, in addition to oxygen. Generally, zeolites having a one dimensional pore structure with a pore size ranging from more than about 0.4 nm to less than about 0.7 nm are useful for the process of this invention. Examples of zeolites suitable for skeletal isomerization include the hydrogen form of ferrierite, SAPO-11, SAPO-31, SAPO-41, FU-9, NU-23, NU-10, ZSM-12, ZSM-22, ZSM-23, ZSM-35, ZSM-48, ZSM-50, MeAPO-11, MeAPO-31, MeAPO-41, MeAPSO-11, MeAPSO-31, MeAPSO-41, ELAPO-11, ELAPO-31, ELAPO-41, ELAPSO-11, ELAPSO-31, ELAPSO-41, laumontite, clinoptilolite, cancrinite, offretite, hydrogen form of heulindite, hydrogen form of stilbite, and the magnesium or calcium form of mordenite, as described in U.S. Pat. No. 6,111,160, the disclosure of which is herein incorporated by reference. Other suitable zeolites are disclosed in U.S. Pat. No. 5,817,907, U.S. Pat. App. Pub. No. 2002/0019307, and EP 0 501 57.

A skeletal isomerization catalyst comprising a metal oxide or mixed oxides may be used. Suitable metal oxides or mixed oxides include alumina, silica-alumina, zirconia, silica-zirconia, and the like. Examples of these may be found in U.S. Pat. Nos. 2,417,647, 3,558,733, 5,321,195, and 5,659,104.

Although the skeletal isomerization reaction may be carried out in any reactor type, a fixed-bed reactor is preferred. The catalyst is preferably in the form of extrudates, beads, granules, tablets, and the like.

The skeletal isomerization is carried out preferably at 500 to 850 F, more preferably at 600 to 750 F and at a pressure of 15 to 100 psig, more preferably at a pressure of 20 to 60 psig. The gas hourly space velocity is suitably in the range of 50 to 200 per hour.

An isomerized stream is produced from the skeletal isomerization reaction. The isomerized stream comprises $C_4$ olefins, and possibly small amounts of $C_5$ and higher olefins.

The process comprises reacting the isomerized stream with ethylene in the presence of a metathesis catalyst. Metathesis catalysts are well known in the art (see, e.g., U.S. Pat. Nos. 4,513,099, 5,120,894). Typically, the metathesis catalyst comprises a transition metal oxide. Suitable transition metal oxides include those of cobalt, molybdenum, rhenium, tungsten, and mixtures thereof. Conveniently, the catalyst is supported on a carrier. Suitable carriers include silica, alumina, titania, zirconia, zeolites, clays, and mixtures thereof. Silica and alumina are preferred carriers. The catalyst may be supported on a carrier in any convenient fashion, in particular by adsorption, ion-exchange, impregnation, or sublimation. The transition metal oxide constituent of the catalyst may amount to 1 to 30 wt % of the total catalyst, preferably 5 to 20 wt %.

In addition to the metathesis catalyst, the metathesis step preferably uses a double-bond isomerization catalyst. A double-bond isomerization catalyst can convert 1-butene to 2-butenes during the metathesis reaction, thus increase the propylene yield of the metathesis reaction.

Many double-bond isomerization catalysts can be used, including acidic catalysts and basic catalysts. Suitable acidic catalysts include metal oxides (e.g., alumina, zirconia, sulfated zirconia), mixed oxides (e.g., silica-alumina, zirconia-silica), acidic zeolites, acidic clays (see, e.g., U.S. Pat. No. 4,992,613, U.S. Pat. Appl. Pub. Nos. 2004/0249229 and 2006/0084831). The basic double-bond isomerization catalysts are preferably metal oxides such as magnesium oxide (magnesia), calcium oxide, barium oxide, and lithium oxide. Metal oxides supported on a carrier may be used. Suitable carriers include silica, alumina, titania, silica-alumina, and the like, and mixtures thereof (see, e.g., U.S. Pat. Nos. 5,153,165, 5,300,718, 5,120,894, 4,992,612, U.S. Pat. Appl. Pub. No. 2003/0004385). A particularly preferred basic isomerization catalyst is magnesium oxide. Suitable magnesium oxide has a surface area of at least 1 square meters per gram ($m^2/g$), preferably at least 5 $m^2/g$.

The reaction of the isomerized stream with ethylene in the presence of a metathesis catalyst is performed at a pressure that is equal to or lower than the pressure of the skeletal isomerization. Typically, the pressure of the metathesis reaction is conducted at 15 to 100 psig, more preferably at 20 to 60 psig. The advantage of the present invention is that it does not require cooling the isomerized stream, pressurizing it, then heating it up again to a temperature suitable for the metathesis reaction. The invention thus saves energy and equipment. Examples 1 and 2 below further illustrate the advantages of the invention.

The metathesis reaction produces a metathesis product stream that comprises ethylene, propylene, $C_4$ olefins, and $C_5$ and higher olefins ($C_5$+ olefins).

Preferably, the process further comprises separating the metathesis product stream into an ethylene stream, a propylene product stream, a $C_4$ stream (containing mostly $C_4$ olefins), and a $C_5$+ olefins stream. The $C_5$+ olefins stream contains mostly olefins with five or more carbons, which may be used as gasoline blending components. Separation of a mixture like the metathesis product stream is known to a person skilled in the art. See U.S. Pat. No. 7,214,841. Typically, such separation is carried out by utilizing three distillation columns in series: a deethenizer, a depropenizer, and a debutenizer.

The ethylene stream is separated by the deethenizer as an overhead. Typically the deethenizer is operated at a temperature of −5 to 40 F in the condenser and a pressure of 350 to 650 psig. Preferably, the ethylene stream is recycled to the metathesis reaction of the process.

Propylene and any lighter compounds are removed in the overhead of the depropenizer. Typically the depropenizer is operated at a temperature of 50 to 140 F in the condenser and a pressure of 100 to 350 psig.

The $C_4$ olefins and any lighter compounds are removed from the debutenizer as an overhead. Typically the debutenizer is operated at a temperature of 100 to 160 F in the condenser and a pressure of 50 to 140 psig. Preferably, the $C_4$ olefins stream is recycled to the skeletal isomerization reaction of the process. $C_5$ and heavier products are separated as a bottoms of the debutenizer.

Example 1

Figure 1A:
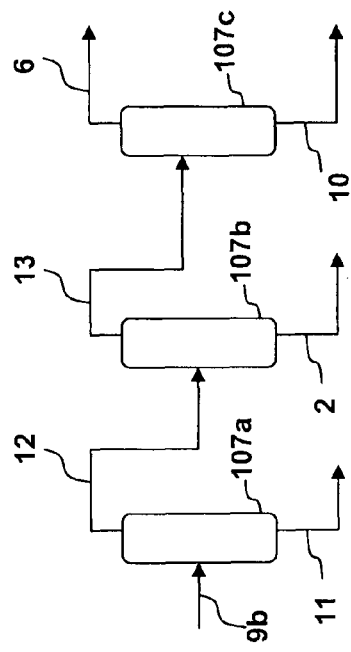
FIG. 1A shows the details of the separation zone of FIG. 1.

The process is shown in FIGS. 1 and 1A. A fresh isobutene feed (100,000 lb/h) in line 1 is combined with a recycled $C_4$ stream from line 2 to form a combined $C_4$ feed in line 3. The combined $C_4$ feed is heated in heating zone 101 to 700 F. The heated combined $C_4$ stream, via line 3a, enters the skeletal isomerization reactor 102 to form an isomerized product stream. An H-Ferrierite catalyst described in Example 1 of U.S. Pat. No. 6,111,160 is used in reactor 102. The isomerization is performed at 700 F and 30 psig. The isomerized stream exits reactor 102 via line 4 at a temperature of 656 F and combines with the fresh ethylene feed in line 5 and a recycled ethylene stream in line 6. The combined feed is heated by heating zone 103 and enters a metathesis reactor 104 via line 8a. The metathesis reactor 104 contains a mixture of magnesium oxide and $WO_3$-on-silica as disclosed in U.S. Pat. No. 5,120,894. The metathesis reaction is performed at 650 F and 30 psig. The metathesis product stream exits the reactor 104 via line 9 and is cooled via cooling zone 105 to 140 F, pressurized by compressor 106, and fed to the separation zone 107 via line 9b.

The details of the separation zone 107 are shown in FIG. 1A. It includes a debutenizer 107a, a depropenizer 107b, and a deethenizer 107c. The order of distillation, from lower pressure to higher pressure, is well suited for a low pressure vapor feed in line 9b. The metathesis product stream enters debutenizer 107a via line 9b. A $C_5+$ olefins stream is recovered as a bottoms stream of debutenizer 107a via line 11. The overhead containing butenes and lighter olefins is fed to the depropenizer 107b via line 12. The butenes stream is obtained as the bottoms of the depropenizer 107b and recycled to the isomerization reaction via line 2. The overhead enters the deethenizer 107c via line 13. An ethylene stream is separated in the deethenizer 107c as overhead in line 6. The propylene product stream is obtained from the bottoms stream via line 10. The expected compositions of various streams are listed in Table 1. The total heat transferred for the process is shown in Table 2.

Comparative Example 2

Figure 2:
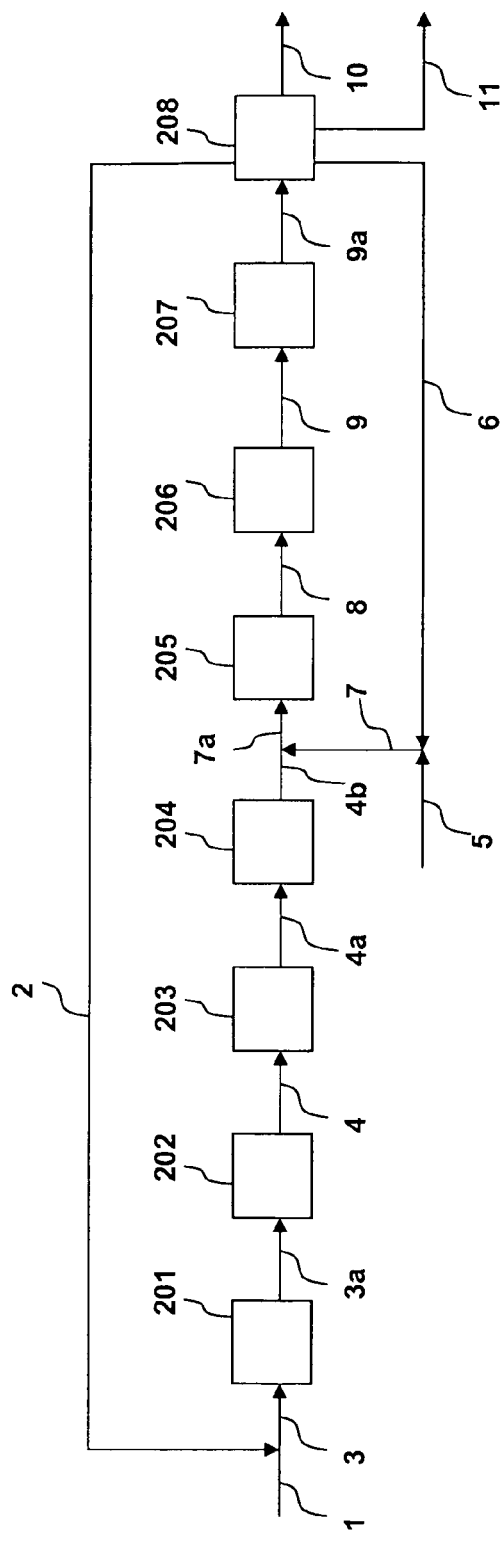
FIG. 2 is a schematic representation of a comparative process for producing propylene.
Figure 2A:
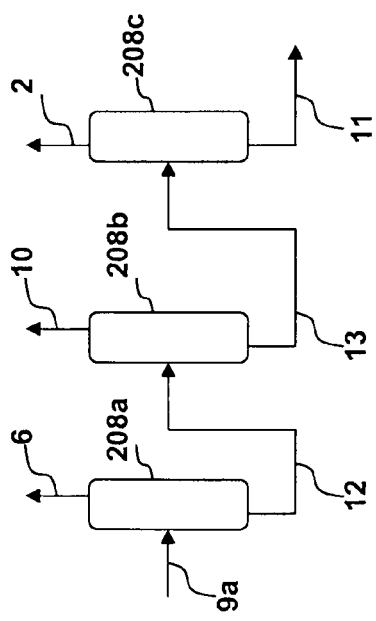
FIG. 2A shows the details of the separation zone of FIG. 2.

The process is shown in FIGS. 2 and 2A. A fresh isobutene feed in line 1 is combined with a recycled $C_4$ stream from line 2 to form a combined $C_4$ feed in line 3. The combined $C_4$ stream is heated by the heating zone 201 to 700 F. The heated $C_4$ feed enters the isomerization reactor 202 via line 3a. An H-Ferrierite catalyst described in Example 1 of U.S. Pat. No. 6,111,160 is used in reactor 202. The isomerized product stream exits the reactor 202 via line 4 and enters cooling zone 203 and is cooled to 80 F. The condensed stream in line 4a is pumped to 450 psig by pump 204, and is mixed with a fresh ethylene feed in line 5, and a recycled ethylene stream from line 6. The mixed feed is heated in zone 205 to 650 F and enters metathesis reactor 206. The metathesis reactor 206 contains a mixture of magnesium oxide and $WO_3$-on-silica as disclosed in U.S. Pat. No. 5,120,894. The metathesis reactor is operated at 650 F and 450 psig. The metathesis product stream in line 9 is cooled via cooling zone 207 and enters the separation zone 208.

The details of the separation zone 208 are shown in FIG. 2A. It includes a deethenizer 208a, a depropenizer 208b, and a debutenizer 208c. The metathesis product stream enters deethenizer 208a via line 9a. The order of distillation, from higher pressure to lower pressure, is well suited for a high pressure feed in line 9a. Unreacted ethylene is recovered as an overhead in deethenizer 208a and is recycled via line 6. The deethenizer bottoms stream containing propylene and $C_4$-$C_6$ olefins is fed to depropenizer 208b, where propylene product stream is recovered as an overhead via line 10. Butenes, $C_5$ olefins, and higher olefins from depropenizer 208b bottoms are fed to debutenizer 208c via line 13, where butenes are separated as overhead and are recycled via line 2. A $C_5+$ olefins stream is recovered as a bottoms product stream from debutenizer 208c via line 11. The expected compositions of various streams are listed in Table 1. The total heat transferred for the process is shown in Table 2.

Table 2 compares the heating and cooling requirements for the two examples, including those required for the separation zones. Energy savings can be realized by heat integrating hot process streams with cold process streams; however, the size and cost of the heat integration equipment increases as the amount of heat integrated increases. By application of this invention (Example 1), the heat integration can be reduced by half, from 398 MMBTU/h to 194 MMBTU/h. The savings in heat integration is from changes in the front end of the process. Furthermore, heating with utilities such as steam or fired heaters is reduced from 218 MMBTU/h to 158 MMBTU/h. Cooling with utilities such as cooling water, air, or refrigeration is also reduced. The savings in utility heating and cooling is from changing the order of distillation, which lends itself to match the lower pressure from metathesis.

TABLE 1

Compositions of Streams in Examples 1 and Comparative Example 2 (lb/h)

| | Stream | | | | | | | | | | |
|---|---|---|---|---|---|---|---|---|---|---|---|
| | 1 | 2 | 3 | 4 | 5 | 6 | 7 | 8 | 9 | 10 | 11 |
| Ethylene | | | | | 39462 | 166964 | 206426 | 206426 | 166965 | 0 | |
| Propylene | | 2583 | 2583 | 2583 | | 1305 | 1305 | 3888 | 130480 | 126591 | |
| Butene-1 | | 3669 | 3669 | 23845 | | | | 23845 | 3681 | 12 | 1 |
| Cis-2-Butene | | 5539 | 5539 | 35224 | | | | 35224 | 5627 | 0 | 89 |
| Trans-2-Butene | | 7463 | 7463 | 46599 | | | | 46599 | 7502 | 0 | 39 |
| Isobutene | 100000 | 89756 | 189756 | 100758 | | | | 100758 | 89757 | 0 | 0 |
| C5+ Olefins | | 1414 | 1414 | 1414 | | | | 1414 | 14143 | | 12729 |
| Total | 100000 | 110424 | 210424 | 210424 | 39462 | 168269 | 207731 | 418155 | 418155 | 126604 | 12857 |

TABLE 2

| Total Heat Transferred | | |
|---|---|---|
| MMBTU/h | Example 1 | Comparative Example 2 |
| Heat Integrated | 194 | 398 |
| Utility Heating | 158 | 218 |
| Utility Cooling | 198 | 225 |

We claim:
1. A process for producing propylene comprising
   (a) reacting a feed stream comprising isobutene in the presence of a skeletal isomerization catalyst to obtain an isomerized stream of isobutene comprising $C_4$ olefins; and
   (b) reacting the isomerized stream with ethylene in the presence of a metathesis catalyst to form a metathesis product stream comprising propylene, $C_4$ olefins, and $C_5$ and higher olefins;
   wherein step (b) is performed at an equal or lower pressure than step (a).

2. The process of claim 1 wherein step (a) is performed at 20 to 60 psig.

3. The process of claim 2 wherein step (b) is performed at 20 to 60 psig.

4. The process of claim 1 wherein the feed stream comprises greater than 95 wt % of $C_4$ olefins.

5. The process of claim 1 wherein the feed stream is produced by dehydration of tert-butyl alcohol.

6. The process of claim 1 further comprising separating the metathesis product stream into an ethylene stream, a propylene product stream, a $C_4$ olefins stream, and $C_5$ and higher olefins stream.

7. The process of claim 6 wherein step (a) is performed at 20 to 60 psig.

8. The process of claim 7 wherein step (b) is performed at 20 to 60 psig.

9. The process of claim 6 wherein the ethylene stream is recycled to step (b).

10. The process of claim 6 wherein the $C_4$ olefins stream is recycled to step (a).

11. The process of claim 6 wherein the feed stream comprises greater than 95 wt % $C_4$ olefins.

12. The process of claim 6 wherein the feed stream is produced by dehydration of tert-butyl alcohol.

13. The process of claim 1 wherein heat integration of the process is reduced compared to a process where step (b) is performed at a higher pressure than step (a).

\* \* \* \* \*